US009308294B2

(12) United States Patent
Cabrera

(10) Patent No.: US 9,308,294 B2
(45) Date of Patent: Apr. 12, 2016

(54) SYNTHETIC SEROUS MEMBRANES AND METHODS FOR MAKING THE SAME

(75) Inventor: Robert Cabrera, Austin, TX (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 13/499,392

(22) PCT Filed: May 5, 2011

(86) PCT No.: PCT/US2011/035322
§ 371 (c)(1),
(2), (4) Date: Mar. 30, 2012

(87) PCT Pub. No.: WO2012/150939
PCT Pub. Date: Nov. 8, 2012

(65) Prior Publication Data
US 2012/0283843 A1 Nov. 8, 2012

(51) Int. Cl.
A61L 27/34 (2006.01)
A61L 27/18 (2006.01)

(52) U.S. Cl.
CPC .............. *A61L 27/34* (2013.01); *A61L 27/18* (2013.01); *A61L 2430/20* (2013.01)

(58) Field of Classification Search
CPC ....... A61L 27/34; A61F 2/105; A61F 2/0063; A61F 2/0077; A61F 2002/0081; A61F 2002/0086

USPC .......... 623/23.72–23.76, 901, 909, 915, 920, 623/924–926; 264/313, 316, 337
See application file for complete search history.

(56) References Cited

U.S. PATENT DOCUMENTS

| 7,084,082 B1* | 8/2006 | Shimizu ................... 442/123 |
| 2004/0234954 A1* | 11/2004 | Nusslein et al. ................... 435/5 |
| 2008/0260801 A1* | 10/2008 | Ahlers et al. ................... 424/426 |
| 2010/0036503 A1 | 2/2010 | Chen et al. |
| 2010/0310628 A1* | 12/2010 | Waldburg-Zeil ............... 424/426 |

FOREIGN PATENT DOCUMENTS

EP 1 577 083 9/2005

OTHER PUBLICATIONS

Bolisay, L. D. et al., "Molecularly imprinted polymers for tobacco mosaic virus recognition," Biomaterials, 2006, vol. 27, pp. 4165-4168.
Glangchai, L. C. et al., "Nanoimprint lithography based fabrication of shape-specific, enzymatically-triggered smart nanoparticles," Journal of Controlled Release, 2008, vol. 125, pp. 263-272.
International Search Report and Written Opinion for PCT/US2011/035322 mailed Jul. 4, 2011.

(Continued)

*Primary Examiner* — Thomas McEvoy
(74) *Attorney, Agent, or Firm* — Foley & Lardner LLP

(57) ABSTRACT

The present disclosure relates to casting-mold imprints and synthetic reproductions of serous membranes for tissue engineering and organogenesis. The imprints and synthetic membranes disclosed herein may be composed of distinct biocompatible polymers, which provide a mechanism for separation. Further disclosed herein are methods for making imprints and synthetic membranes that mimic natural serous membranes.

12 Claims, 2 Drawing Sheets

(56) References Cited

OTHER PUBLICATIONS

Kanzaki, M. et al., "Functional closure of visceral pleural defects by autologous tissue engineered cell sheets," Eur. J. Cardiothorac Surg., 2008, vol. 34, pp. 864-869.

Kuga, H. et al., "Construction of a Transplantable Tissue-Engineered Artificial Peritoneum," Eur. Surg. Res., 2004, vol. 36, pp. 323-330.

Lee, W. et al., "Multi-layered culture of human skin fibroblasts and keratinocytes through three-dimensional freeform fabrication," Biomaterials, 2009, vol. 30, pp. 1587-1595.

Schwarz, W., "The surface film on the mesothelium of the serous membranes of the rat," Z Zellforsch Mikrosk Anat., 1974, vol. 147, pp. 595-597.

Vozzi, G. et al., "Soft-Mi: A Novel Microfabrication Technique Integrating Soft-Lithography and Molecular Imprinting for Tissue Engineering Applications," Biotechnology and Bioengineering, Aug. 1, 2010, vol. 106, No. 5, pp. 804-817.

Xia, Y-Q. et al., "Hemoglobin Recognition by Imprinting in Semi-Interpenetrating Polymer Network Hydrogel Based on Polyacrylamide and Chitosan," Biomacromolecules, 2005, vol. 6, pp. 2601-2606.

* cited by examiner

SYNTHETIC SEROUS MEMBRANES AND METHODS FOR MAKING THE SAME

CROSS REFERENCE TO RELATED APPLICATIONS

This application is the U.S. national stage application under 35 U.S.C. §371 of International Patent Application No. PCT/US2011/035322, filed on May 5, 2011, the contents of which are incorporated herein by reference in their entireties.

TECHNICAL FIELD

The present disclosure relates generally to synthetic serous membranes and molecular imprints for the production thereof. In particular, the present disclosure includes imprinted serous membrane casting-molds, which can form synthetic serous membranes that are capable of inducing cellular differentiation.

BACKGROUND

The following description is provided to assist the understanding of the reader. None of the information provided or references cited is admitted to be prior art.

Organ regeneration and tissue engineering involve the manipulation of living cells to develop biological substitutes for patients in need thereof. In order for tissue and organ replacement to be practical, however, the framework for producing such complex biological structures must imitate an environment that can guide natural cell differentiation and tissue growth. Natural or artificial scaffolds, i.e., matrix complexes, can support a variety of cellular and tissue related processes. These biological structures serve multiple purposes, including, facilitating cell or tissue attachment, migration, delivery, and retention. As such, biological scaffolds can be seeded with cells and cultured in vitro or directly implanted into a patient. However, three-dimensional tissue engineering and organ development requires additional considerations relating to scaffold topology.

Tissue engineering applications may require structures that can support cell development for a variety of different cell-types, including stem cells. In this regard, precise topological reproductions of membranous structures, which biologically mimic actual membranes, can guide sterically-induced cellular differentiation and subsequent organogenesis. Accordingly, authentic membrane support complexes are necessary for ensuring the development and integrity of specific tissues by providing the proper topological environment. Additionally, mechanisms for reproducing such support complexes are an important consideration in the development of new strategies for large-scale tissue engineering and organ replacement.

SUMMARY

In one aspect, the present disclosure provides a casting-mold for a synthetic serous membrane composed of one or more biocompatible polymers that form a topological imprint of a serous membrane. In one embodiment, the one or more biocompatible polymers are gelatin, agarose, chitin, chitosan, polyglycolic acid, polylactic acid, polylactide-glycolide, or polydioxanone, or any combination thereof. In one embodiment, the imprint is a synthetic pericardial, pleural, or peritoneal membrane imprint, or any combination thereof In one embodiment, the synthetic pericardial, pleural, or peritoneal membrane imprint includes a two-layer imprint. In one embodiment, the two-layer imprint is an imprint of a synthetic visceral and parietal layer.

In one aspect, the present disclosure provides a synthetic serous membrane including one or more biocompatible polymers that form a topological reproduction of a serous membrane. In one embodiment, the one or more biocompatible polymers are gelatin, agarose, chitin, chitosan, polyglycolic acid, polylactic acid, polylactide-glycolide, or polydioxanone, or any combination thereof. In one embodiment, the reproduction is capable of facilitating cellular differentiation, cell attachment, cell growth, cell-sheet growth, tissue growth, tissue engineering, or encasing tissues or organs, or any combination thereof.

In one embodiment, the reproduction is a synthetic pericardial, pleural, or peritoneal membrane, or any combination thereof In one embodiment, the synthetic pericardial, pleural, or peritoneal membrane includes a two-layer membrane. In one embodiment, the two-layer membrane includes a synthetic visceral and parietal layer.

In one aspect, the present disclosure provides a method for making a casting-mold for a serous membrane by applying one or more biocompatible polymers to a serous membrane to form a topological imprint, wherein the topological imprint is formed within a hydrogel casting-mold, and fixing the imprint, and separating the serous membrane from the imprint. In one embodiment, the biocompatible polymers are gelatin, agarose, chitin, chitosan, polyglycolic acid, polylactic acid, polylactide-glycolide, or polydioxanone, or any combination thereof.

In one embodiment of the method, the imprint is a synthetic pericardial, pleural, or peritoneal membrane imprint, or any combination thereof In one embodiment of the method, the synthetic pericardial, pleural, or peritoneal membrane imprint includes a two-layer imprint. In one embodiment of the method, the two-layer imprint is an imprint of a synthetic visceral and parietal layer. In one embodiment, the fixing is by cross-linking or temperature change.

In one aspect, the present disclosure provides a method for producing a synthetic serous membrane by adding one or more biocompatible polymers to a topological imprint of a serous membrane to form a synthetic serous membrane, and removing the synthetic serous membrane from the imprint. In one embodiment of the method, the one or more biocompatible polymers are gelatin, agarose, chitin, chitosan, polyglycolic acid, polylactic acid, polylactide-glycolide, or polydioxanone, or any combination thereof In one embodiment of the method, the imprint is a synthetic pericardial, pleural, or peritoneal membrane imprint, or any combination thereof.

In one embodiment of the method, the synthetic pericardial, pleural, or peritoneal membrane imprint includes a two-layer imprint. In one embodiment of the method, the two-layer imprint is an imprint of a synthetic visceral and parietal layer. In one embodiment of the method, the one or more biocompatible polymers is a different polymer than a polymer used to form the imprint. In one embodiment of the method, the removing is by physical, enzymatic, or chemical methods. In one embodiment, the physical method is by a change in temperature or pressure, or both. In one embodiment of the method, the imprint remains intact following the removing.

In one aspect, the present disclosure provides a method for tissue engineering including forming a synthetic serous membrane from one or more biocompatible polymers, and culturing cells on or within the synthetic serous membrane to form one or more cell-layers, tissues, or organs. In one embodiment, the methods further include harvesting the one or more cell-layers, tissues, or organs. In one embodiment, the one or more cell-layers, tissues, or organs are suitable for cell and tissue grafting, skin-grafting, allografting, wound healing grafts, skin replacement, ocular reconstruction, liver tissue reconstruction, cardiac patching, organ transplant, or bladder augmentation, or any combination thereof.

In one embodiment of the method, the one or more cell-layers is a monolayer. In one embodiment, the one or more cell-layers are stratified layers. In one embodiment, the stratified layers are different cell-types. In one embodiment, the stratified layers form whole organs, partial organ masses, spheroid cell-bodies, tubular cell-bodies, hollow cell-bodies, graded porosity masses, or solid masses, or any combination thereof.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1:
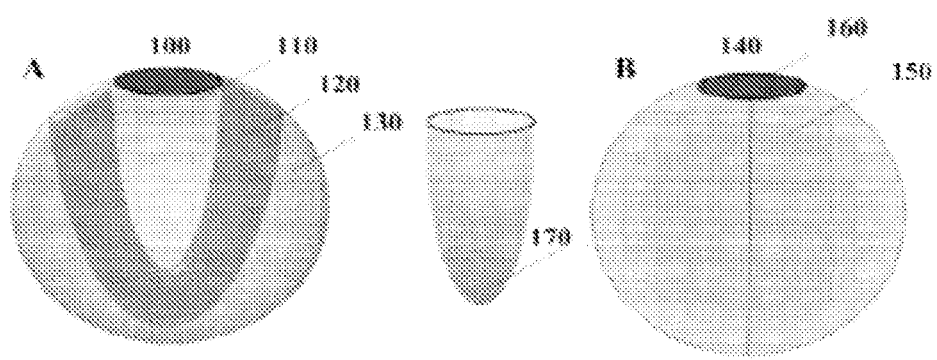
FIGS. 1A-1B are illustrative embodiments of a serous membrane and components that can be employed for synthetic reproductions thereof, respectively.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used herein, unless otherwise stated, the singular forms "a," "an," and "the" include plural reference. Thus, for example, a reference to "a tissue" or "the tissue" includes a plurality of tissues.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein, the term "biocompatible" polymer refers to a synthetic or natural material that is compatible, i.e., non-toxic, to biological systems. A biocompatible polymer may also possess biodegradable properties, although biodegradability is not necessarily a characteristic of a "biocompatible" polymer.

As used herein, the term "biodegradable" polymer refers to a synthetic or natural material that will degrade, i.e., break down, when exposed to, or placed in the presence of an appropriate solvent. The rate of degradation may be fast, e.g., degradation may take place in minutes, or slow, e.g., degradation may take place over hours, days, weeks or months, or the polymer may degrade in response to a particular solvent concentration. In some embodiments, the rate of degradation can be controlled by the type of solvent and/or polymer that is used. A biodegradable polymer may also be biocompatible.

As used herein, the terms or "casting-mold" or "impression" or "imprint" or "molecular imprint", used in the context of tissue engineering, serous membrane reproduction, and/or hydrogel preparation, refer to any surface or structure created that is capable of reproducing a serous membrane including any ancillary cells and/or tissues grown therewith. Such casting-molds or imprints have various contemplated surfaces, and/or are composed of materials, which include, but are not limited to, polymers, biocompatible polymers, biodegradable polymers, copolymers, terpolymers, hydrogels, and the like.

As used herein, the terms "hydrogel" or "gel" or "hydrogel matrix" are used interchangeably, and encompass polymer and non-polymer based hydrogels, including, but not limited to, e.g., poly(hyaluronic acid), poly(sodium alginate), poly(ethylene glycol) (PEG), poly(glycolic acid) polymers, poly(lactide-co-glycolides) (PLGA), poly(urethanes), poly(siloxanes), silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(methacrylic acid), polylactic acid (PLA), polyglycolic acids (PGA), nylons, polyamides, polyanhydrides, poly(ethylene-co-vinyl alcohol) (EVOH), polycaprolactone, polyvinylhydroxide, poly(ethylene oxide) (PEO), polyorthoesters, and/or copolymers or terpolymers formed from at least two or three members of the foregoing polymers, respectively. Also used herein, the terms "tissue matrix" or "tissue hydrogel" similarly refer to any composition formed into a porous matrix into which cells or tissue can grow in three dimensions. Hydrogels are typically continuous networks of hydrophilic polymers that absorb water.

As used herein, the term "organ" refers to a part or structure of the body, which is adapted for a special function or functions, and includes, but is not limited to, the skin, the lungs, the liver, the kidneys, and the bowel, including the stomach and intestines. In particular, it is contemplated that organs which are particularly susceptible to dysfunction and failure arising from an injury are amenable to tissue-engineered reconstruction and are encompassed by the term "organ." "Tissues" are singular or multiply-layered structures, i.e., monolayers or stratified layers of cells, which are organ constituents. One or more different tissues may form an organ or organs. An organ may also be composed of only one type of tissue or cell.

As used herein, the term "serous membrane" refers to any and all membranes known as such in the art. A serous membrane typically surrounds an organ or biological structure, thereby encasing and separating the tissue from other organ macroenvironments.

Synthetic Serous Membranes and Tissue Engineering Applications

In vivo, cells are structured within a complex matrix composed of fibrous proteins and polysaccharides known as the extracellular matrix or ECM. The ECM is a three-dimensional network that includes the interstitial matrix and basement membrane layer. One of the defining features of the ECM is its ability to direct the growth, organization, and differentiation of various cell types. Accordingly, simulating interactions that occur between cells and the ECM is a precept of tissue regeneration. Consequently, tissue and organ development depend, in part, upon accurately reproducing the structural features that guide such interactions.

The native cellular microenvironment contains a myriad of morphological and topological features, e.g., cell-cell junctions, ligand-receptor complexes, etc., which influence the fate of pluripotent stem cells and multipotent progenitor cells. In order to reproduce this microenvironment, tissue engineering substrates must have an appropriate and well-defined structure in order to facilitate cellular differentiation and proliferation. The topological features of multi-dimensional structures for cell culture applications, including tissue and/or organ generation, can be artificially reproduced using several procedures known in the art. See, e.g., Xia et al., *Hemoglobin Recognition by Imprinting in Semi-Interpenetrating Polymer Network Hydrogel Based on Polyacrylamide and Chitosan. Biomacromolecules.* Vol. 6, 2601-2606 (2005). Briefly, these techniques allow for the production of highly specific synthetic polymers, which accurately reflect the original topological substrate. Molecular imprinting or molecular mimicry is one such technique.

Molecular imprinting allows for the topological reproduction of a substrate by employing nano- or micro-scale monomers capable of coating the surface of a substrate, such as, e.g., biological membranes. These monomeric constituents, e.g., acrylamide, can self-assemble on the substrate via covalent or non-covalent interactions. Prior to polymerization, the monomers are applied to the substrate surface in thin layers, which coordinately cover, and thereby imprint, the surface topology of the substrate. The application process is designed to facilitate the authentic fabrication of substrates that vary in size, shape, polarity, and/or functionality.

Following polymerization in the presence of a suitable crosslinking agent, the substrate is separated or removed from the resulting construct, i.e., the molecular imprint. This framework structure constitutes a highly specific complementary impression of the original substrate, and can be used as a template or casting-mold for synthetic reproductions of native biological structures. In this regard, prior to cell culturing, the molecular imprint may also be coated with serous fluid (e.g., glucosaminoglycans) to mimic the endogenous lubrication and environment of a serous membrane. See, e.g., Schwarz, W., The Surface Film on the Mesothelium of the Serous Membranes of the Rat. *Z. Zellforsch.* Vol. 147, p. 595-597 (1974).

Various biocompatible polymers or matrices can be employed for imprinting applications that relate to cell and tissue-based constructs. In suitable embodiments, biocompatible matrices are composed of hydrogel polymers. Hydrogels are hydrophilic structures composed of homopolymers or co-polymers, which provide an environment for cells to grow and correspondingly drive the process of tissue formation in three dimensions. Synthetic polymers are attractive matrix materials because they can be readily manufactured with a wide range of reproducible, biocompatible structures. These matrix structures can vary in composition, while still providing sufficient mechanical support for withstanding compressive and/or tensile forces. In this regard, maintaining the shape and integrity of the matrix is essential for tissue engineering applications such as molecular imprinting.

A range synthetic polymers can be utilized for molecular imprinting of cell and tissue structures. These materials include, but are not limited to, poly(hyaluronic acid), poly(sodium alginate), poly(ethylene glycol) (PEG), diacrylate, chitosan, poly(vinyl alcohol) (PVA), poly(glycolic acid) (PGA), poly(lactic acid) (PLA), poly lactic co-lactic acid (PLLA), poly(lactic acid)-poly(glycolic acid) (PLGA), gelatin, agarose, chitin, chitosan, and/or polydioxanone. These polymers are also extensively used in biomedical applications such as drug delivery and are FDA approved for a variety of applications. A number of other synthetic biocompatible matrices are also known in the art. See, e.g., Vozzi et al., *SOFT-MI: A Novel Microfabrication Technique Integrating Soft-Lithography and Molecular Imprinting for Tissue Engineering Applications. Biotechnology and Bioengineering,* Vol. 106 (5) (2010).

Biocompatible matrices provide a native-like biological milieu for cell differentiation and tissue development at the micro- and macromolecular scale. In this regard, certain molecular imprinting applications provide for the production of multi-layered, cell-hydrogel composites on non-planar surfaces, such as skin wound repair. See, e.g., Lee et al., *Multi-layered culture of human skin fibroblasts and keratinocytes through three-dimensional freeform fabrication. Biomaterials.* Vol. 30, 1587-1595 (2009). Accordingly, the reproduction of entire higher-order structures, including multilayered biological membranes, e.g., serous membranes, for tissue or organ development, is supported by the use of biocompatible polymers via molecular mimicry.

Serous membranes, also termed serosa, are biological tissues that prevent cellular and tissue adhesion between organs, thereby allowing the organs to freely move relative to one another. These membranes are characterized by a single layer of mesothelial cells attached to the surface of a thin layer of collagenous tissue, which is connected to the underlying endothoracic-transversalis fascia. Serous membranes can be found encompassing organs such as, but not limited to, the heart, liver, intestines, and lungs.

The precise reproduction of serous membranes requires developing an imprint of the entire membrane. To this point, serous membranes have two-layers—an outer layer, the parietal layer, which is attached to the surrounding tissues, and an inner layer, the visceral layer, which is attached to the organ that it encases. Typical examples of serous membranes, include the peritoneum, the pleura, and the pericardium, which envelope the intestines, lungs, and heart, respectively. In view of the complex organization of serous membranes, molecular mimicry provides a useful tool for authentic reproductions of these multifarious biological structures.

In one aspect, the present disclosure provides a casting-mold, capable of facilitating synthetic serous membrane production, composed of one or more biocompatible polymers. The biocompatible polymers form a topological imprint of the serous membrane, thereby maintaining the morphological structure the native membrane. In suitable embodiments, the biocompatible polymer is gelatin, agarose, chitin, chitosan, polyglycolic acid, polylactic acid, polylactide-glycolide, and/or polydioxanone. The casting-mold imprint is suitable for single or multilayer, e.g., two-layer, synthesis of pericardial, pleural, and/or peritoneal serous membranes, among others. In this regard, the two-layer imprint is a synthetic impression or mold of the visceral and parietal layers.

Initially, a donor serous membrane is obtained as a template for the production of synthetic serous membrane imprints. In this respect, direct implantation of donor serous membranes, into patients, is not feasible for a variety of reasons, such as, but not limited to, lack of a donor-recipient match, organ and tissue rejection, and/or disease transmission. Moreover, the present disclosure provides a mechanism for the reproduction of numerous synthetic serous membranes by first developing a mold, whereas direct implantation would only allow for single-implantation applications.

Once the donor or template membrane has been obtained, it is prepared for imprinting. In suitable embodiments, the membrane is dissected into its constituent or composite layers, i.e., the parietal and visceral layers, prior to applying the biocompatible polymer. In another embodiment, the entire serous membrane is left intact. A first polymer is then applied to the serous membrane to produce the imprint. This polymer can be, for example, gelatin, agarose, chitin, chitosan, polyglycolic acid, polylactic acid, polylactide-glycolide, and/or polydioxanone. Subsequently, the imprint may be physically or chemically sterilized, thereby providing a sterile template to manufacture synthetic serous membranes for clinical applications.

Various degrees of thickness are envisaged for the polymer layer. The skilled artisan will readily appreciate that different levels and degrees of polymer thickness can be applied for a variety of intended polymer applications. In this regard, the thickness of the biocompatible polymer layer can be from about 0.01-900, 0.1-100, 0.1-70, 1-50, or 15-30 nm. In suitable embodiments, the thickness of the biocompatible polymer layer is from about 15-30 nm.

To ensure that the proper topological environment is reproduced, after membrane application, the polymer is fixed and/or stabilized. In one embodiment, the polymer is fixed by crosslinking using suitable crosslinking agents such as, but not limited to, methylenebisacrylamide, divinylbenzene, formaldehyde, paraformaldehyde, ethylene glycol di(meth)acrylate, and derivatives thereof, EDC, SMCC, MBS, SMPB, Sulfo-SMPB, GMBS, and/or Sulfo-GMBS, and the like. In another embodiment, the polymer is fixed and/or stabilized via solidification by allowing the polymer to cool to a suitable temperature. The biocompatible polymer, e.g., a hydrogel, can be allowed to solidify or congeal for predetermined lengths of time.

In general, hydrogels can congeal in minutes, hours, days, or weeks. In one embodiment, the hydrogel is allowed to congeal from about 0.1-100, 0.5-90, 1-80, 1.5-70, 2-60, 2.5-55, 3-50, 3.5-40, 4-30, 4.5-20, 5-15, or 6-7 hours (h). In another embodiment, the hydrogel is allowed to congeal from about 6-7 h. It will be readily apparent to the skilled artisan that numerous additional variables can effect hydrogel polymerization, solidification, or congealing. These factors such as, for example, humidity, $CO_2$ concentration, and/or temperature, etc., are contemplated, such that appropriate adjustments can optimize cell and tissue production.

The rigidity of the resulting imprint is sufficient to allow for manipulation and handling thereof. As such, the imprint is peeled away from the underlying serous membrane template, thereby forming a cavernous structure capable of molding a mimic of the template membrane. This serous membrane casting-mold may be a conjoined structure, which includes both the parietal and visceral layers. Conversely, when the serous membrane has been previously dissected, the casting-mold may contain more than one component (see FIG. 1B). Regardless of the composite nature of the imprint, the casting-mold provides a reusable or disposable scaffolding for the production of synthetic serous membranes.

In one aspect, the present disclosure provides a synthetic serous membrane composed of one or more biocompatible polymers that form a topological reproduction of a serous membrane. The synthetic serous membrane may be formed from various different biocompatible polymers such as, but not limited to, gelatin, agarose, chitin, chitosan, polyglycolic acid, polylactic acid, polylactide-glycolide, and/or polydioxanone. However, in one embodiment, the synthetic serous membrane is composed of a different polymer than the material used to produce the casting-mold imprint. By varying the polymers that form the imprint and the synthetic membrane reproduction, a mechanism for separating the complementary structures is provided. Different biocompatible polymers will have diverse properties, such as, for example, solvent degradability, melting point, and the like.

In another embodiment, the imprint and the synthetic reproduction are manufactured from the same polymer. The chemical stability of the imprint polymer eliminates melding with the polymer that forms the reproduction, and a difference in physical or chemical properties imparts a mechanism for separation of the polymers. These differences can be established by a variety of methods, for example, the imprint polymer can contain a higher concentration (e.g. 50% w/v) of the same biocompatible polymer compared to the reproduction polymer (e.g. 25% w/v) and/or the imprint polymer can have a greater degree of cross-linking compared to the reproduction polymer. This allows for differences in melting temperatures between the imprint and synthetic reproduction polymer, thereby eliminating polymer fusion.

In this respect, the present disclosure provides an imprint, complementary to the topology of a native serous membrane, composed of a first biocompatible polymer, which is subsequently employed as a casting-mold for the production of a synthetic replication of the original membrane manufactured out of a second biocompatible polymer. In short, the synthetic serous membrane is formed by applying a specific biocompatible polymer to the casting mold in suitable amounts. The skilled artisan will readily appreciate that different concentrations, levels, degrees, and/or amounts of the biocompatible polymers can be used to form the synthetic serous membrane, and can be applied for a multitude of desired applications.

In order to enable the accurate reproduction of a serous membrane, the synthetic biocompatible polymer can be crosslinked, cooled, or allowed to solidify as described herein. The polymer is typically a biocompatible hydrogel capable of congealing in minutes, hours, days, or weeks. In one embodiment, the hydrogel used to form the synthetic membrane is allowed to congeal from about 0.1-100, 0.5-90, 1-80, 1.5-70, 2-60, 2.5-55, 3-50, 3.5-40, 4-30, 4.5-20, 5-15, or 6-7 h. In another embodiment, the hydrogel used to form the synthetic membrane is allowed to congeal from about 6-7 h. It will be readily apparent to the skilled artisan that different degrees of rigidity will be required for different membrane structures, and adjustments can be made as required.

As described herein, the composite nature of the imprint-reproduction structure imparts a suitable means for physical, enzymatic, and/or chemical removal or separation. In one embodiment, the imprint, i.e., casting-mold, is peeled away from the encased synthetic reproduction. As such, the casting mold can be reused for the manufacture of multiple serous membrane reproductions. In another embodiment, the casting-mold is dissolved by employing a solvent capable of degrading the first polymers, i.e., the imprint, while not affecting the second polymer that was used to form the synthetic membrane. For example, a first polymer of polylactic acid (PLA) can be used to form a secondary polymer of high molecular weight polyglycolic acid (PGA), and, subsequently, when dichloromethane is applied to both polymers, the PLA will dissolve while leaving the PGA intact.

In some embodiments, the removal can be performed by an induced change in atmospheric pressure, such that the pressure differentiation severs the imprint from the synthetic reproduction. The imprinted structure is also contemplated as a readily disposable, biodegradable casting-mold. These imprinted polymers may have lower melting temperatures than the polymers used to form the synthetic membranes, and thus, can be heated to such a degree that they are liquefied, while leaving the synthetic membrane reproduction in an intact solid state.

Since the serous membrane reproduction is a topological duplicate of the original serous membrane, and is composed of biocompatible materials, it is thereby capable of facilitating sterically-induced cellular differentiation, i.e., differentiation that is dependent upon a certain topological and spatially-related stimuli, cell attachment, cell growth, cell-sheet growth, tissue growth, tissue engineering, and/or membrane formation, e.g., serous membranes. In this regard, the present disclosure also provides for the generation of whole tissue and/or organ structures developed from the synthetically created serous membranes.

In general, tissue and/or organ engineering is facilitated by the reproduction of synthetic serous membranes. In suitable embodiments, the synthetic serous membrane is a pericardial, pleural, and/or peritoneal membrane, with one or more layers. In one embodiment, the pericardial, pleural, and/or peritoneal membranes are two-layered membranes, i.e., they include a parietal and visceral layer. Accordingly, through culturing, differentiation, and proliferation of suitable cell types, various tissues and/or organs can be produced from their attendant synthetic serous membranes.

In one aspect, the present disclosure provides a method for tissue engineering that includes forming a synthetic serous membrane from one or more biocompatible polymers, and culturing cells on or within the synthetic serous membrane to form one or more cell-layers, tissues, or organs. In this respect, the synthetic serous membranes are composed of biocompatible polymers, i.e., hydrogel matrices, that are capable of facilitating tissue growth, cell growth, and/or cell-sheet growth. However, cellular proliferation depends upon numerous factors including, but not limited to, the type of cell culture, the frequency of sub-culturing, the type of media employed and how often is it replenished, and the length of time the cells are cultured, the type of membrane, etc.

Cell culturing may be performed and modified, as desired, for suitable cell growth, density and/or confluence, which can be for about 1, 2, 3, 4, 5, 6, 7, 8, 9, 10, 11, 12, 13, 14, 15, 16, 17, 18, 19, 20, 25, 30, 35, 40, or 50 days. In some embodiments, the cells are cultured for about 13, 14, 15, 16, 17, or 18 days. In one embodiment, the cells are cultured until a desired cell density is attained. In one embodiment, the cells are cultured until they are grown to confluence. The amount of time required for cell culturing may depend upon the type of cell cultured. In one embodiment, the synthetic serous membrane is submerged in cell/tissue culture media for a desired length of time or until a desired tissue or organ is produced. Cell culture media, e.g., DMEM, can be replenished as required for suitable cell and tissue growth.

Serous membrane tissue engineering further includes producing tissues that emanate from one or more various cell-types. As such, it is contemplated that different cell-types can be employed for the methods disclosed herein, which include, but are not limited to, human or mammal skin cells, muscle cells, epithelial cells, endothelia cells, stem cells, umbilical vessel cells, corneal cells, cardiomyocytes, aortic cells, corneal epithelial cells, aortic endothelial cells, fibroblasts, hair cells, keratinocytes, melanocytes, adipose cells, bone cells, osteoblasts, airway cells, microvascular cells, mammary cells, vascular cells, chondrocytes, and/or placental cells.

In addition to diverse cell-types, a variety of cell or tissue applications can be implemented in accord with the present methods. These applications include, but are not limited to, producing cell-layers and/or tissues that are suitable for cell and tissue grafting, skin-grafting, allografting, wound healing grafts, skin replacement, ocular reconstruction, liver tissue reconstruction, cardiac patching, whole organ regeneration, bladder augmentation, membrane reproduction, or any combination thereof.

Furthermore, one or more cell-layers, cells, tissues, and/or other biological outgrowths can be produced from the methods disclosed herein, and include, but are not limited to, monolayers, stratified layers, spheroid cell-bodies, tubular cell-bodies, hollow cell-bodies, graded porosity masses, and/or solid masses, or any combination thereof. These methods are suitable for cell and tissue engineering, as well as cell immobilized applications relating thereto.

Tissue engineering is enhanced by the membrane reproductions of the present disclosure insofar as they allow for cell and tissue growth, such that the products produced therefrom can be harvested in a non-invasive manner. In this regard, the cells, tissues, organs, and/or other biological products are harvested prior to use. Harvesting tissues may include separation of the hydrogel matrix from cells, tissues, and/or organs developed therewith. Various methods for separating synthetic hydrogel matrices from such biological structures are known in the art and may include proteolytic cleavage, competitive binding, and/or molecular degradation of the hydrogel, etc. In one embodiment, the biocompatible hydrogel does not need to be separated from the biological structures produced therewith prior to patient implantation. In another embodiment, the biocompatible hydrogel is harvested.

FIG. 1A shows an illustrative embodiment of a serous membrane. The serous membrane 100, is formed though the invagination of the membrane 100 upon itself. The inner membrane 110, is also known as the visceral serous membrane 110. A fluid filled space 120, termed the serous cavity 120, is positioned between the outer membrane 130, also known as the parietal serous membrane 130, and the visceral serous membrane 110. In a host organism, these membranous structures surround organs and tissues, such as the heart, lungs, and internal gastrointestinal organs.

FIG. 1B shows an illustrative embodiment of the casting-mold 140 that may be used in accordance with the present disclosure. In a casting-mold 140, the shape and topology of the serous membrane 100 can be reproduced. In the casting-mold 140, an outer shell 150 provides the structural framework for serous membrane production. In the casting-mold 140, an interior biocompatible layer 160 is a topological imprint that was formed in the presence of a parietal serous membrane 130. In the casting-mold 140, a solid insert 170 composed of a biocompatible polymer, i.e., hydrogel, is an imprint that was formed in the presence of visceral serous membrane 110. The biopolymers are applied to the imprints such that the imprinted surfaces contact a biocompatible polymer used to form the synthetic serous membrane. The biocompatible hydrogel matrix is also suitable for cell proliferation, tissue construction, and/or organogenesis. In the casting-mold 140, the cells are grown to a desired density and/or form a desired tissue construct on the hydrogel matrix.

Figure 2:
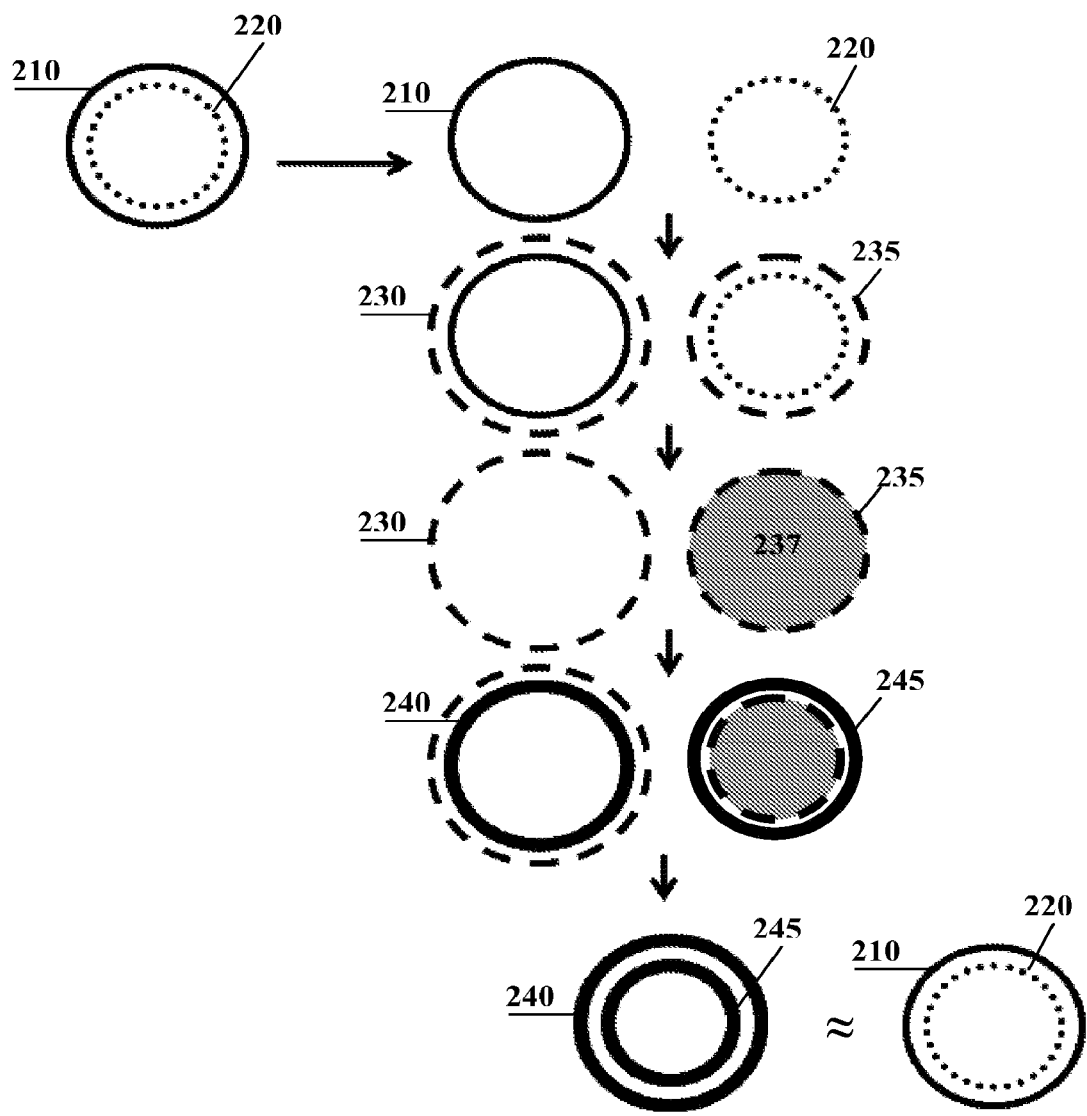
FIG. 2 shows a flow chart of an illustrative embodiment of the process for developing a synthetic serous membrane.

FIG. 2 shows a diagrammatic flow-chart of an illustrative embodiment for the process of developing a synthetic serous membrane. In an operation 200, donor parietal 210 (solid lines) and visceral 220 (dotted lines) serous membrane layers are obtained and dissected. In a membrane 210, the parictial serous membrane 210 is coated in a first biocompatible polymer 230 (dashed lines). In a membrane 220, the visceral serous membrane 220 is coated in the same first biocompatible polymer 235 (dashed lines). In a membrane 230, the parietal serous membrane 210 is removed, leaving a biocompatible imprint 230 of the parietal serous membrane 210. In a membrane 230, the visceral serous membrane 220 is removed, leaving a biocompatible imprint 235 of the visceral serous membrane 220. In a membrane 235, the biocompatible imprint 235 of the visceral serous membrane 220 is a solid structure 237 (filled circle).

In a membrane 230, the interior of the biocompatible imprint 230 of the parietal serous membrane 210, is coated with a second biocompatible polymer 240 (thick lines). In a membrane 235, the interior of the biocompatible imprint 235 of the visceral serous membrane 220, is coated with the same second biocompatible polymer 245 (thick lines). In a membrane 240, a synthetic reproduction is formed of a parietal serous membrane 240 and the visceral serous membrane 245. This synthetic reproduction 240, 245, is a molecular mimic of the original serous membrane 210, 220.

EXAMPLES

The present compositions and methods will be understood more readily by reference to the following examples, which are provided by way of illustration and are not intended to be limiting in any way.

Example 1

Preparation of a Synthetic Serous Membrane

A donor serous membrane is obtained as a template for producing one or more synthetic membrane imprints. The imprint is prepared from either an intact multi-layered membrane or a membrane that constitutes separate parietal and visceral layers. In this regard, the donor membrane may be dissected using tissue forceps or scissors. Subsequently, a polymer is topically applied to the individual parietal and visceral layers, thereby producing an imprint of each layer (see FIG. 1). An imprint may also be produced from an intact donor membrane by submerging the entire membrane into a liquid polymer, which is allowed to coat the membrane surface. In either case, an appropriate polymer is selected from Table 1, applied to the donor template, and allowed to congeal.

TABLE 1

Polymer Applications
POLYMERS

Gelatin; Agarose; Chitin; Chitosan; Polyglycolic acid; Polylactic acid; Polylactide-glycolide; Polydioxanone; Poly(hyaluronic acid); Poly(sodium alginate); Poly(ethylene glycol); Poly(lactic acid); Poly(glycolic acid); Poly(lactide-co-glycolides); Poly(urethanes); Poly(siloxanes); Poly(ethylene); Poly(vinyl pyrrolidone); Poly(2-hydroxy ethyl methacrylate); Poly(N-vinyl pyrrolidone); Poly(methyl methacrylate); Poly(vinyl alcohol); Poly(acrylic acid); Poly(vinyl acetate); polyacrylamide; Poly(ethylene-co-vinyl acetate); Poly(methacrylic acid); Nylons; Polyamides; Polyanhydrides; Poly(ethylene-co-vinyl alcohol); Polycaprolactone; Polyvinylhydroxide; and Poly(ethylene oxide).

Briefly, under sterile conditions, a polylactic acid (PLA) solution is employed at a final concentration of 2.5% (w/v). The PLA solution is applied to the donor membrane template and allowed to congeal for 20 hours. After the synthetic imprint is formed, the donor membrane can be removed. To the extent that a dissected donor membrane was used, the membrane is physically removed from each constituent layer, i.e., peeling the imprint from the dissected donor membrane layers (see FIG. 1). Organic solvents may also be applied to degrade one or both dissected donor membrane layers as described below. When an intact membrane is employed as an imprint template, physical removal is precluded due to the structural confines of a serous membrane. In this case, the donor membrane is dissolved using organic solvents, such as methanol or acetone. Other detergents or lysis buffers such as, e.g., saponin, Triton X-100, RIPA buffer, NP-40, deoxycholate, and Tween-20 may also be employed as degradative solvents for membrane removal.

Following polymer solidification and removal of the donor membrane, a second polymer is applied to the PLA imprint (see Table 1). Under sterile conditions, polyglycolic acid (PGA) is added to the imprint at a final concentration of 2.5% (w/v) and allowed to congeal for 24 hours. Subsequently, dichloromethane is applied to both polymers, thereby dissolving the PLA, while leaving the PGA unaffected. Hexafluoroisopropanol may also be employed as the solvent when dissolving PGA is desired, i.e., when PGA is the imprint polymer. Any residual solvent is subsequently removed via vacuum drying. Alternatively, PLA may be removed by differential melting, e.g., melting PLA from about 175-224° C., thereby leaving the PGA synthetic reproduction intact.

* * * *

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 proteins refers to groups having 1, 2, or 3 proteins. Similarly, a group having 1-5 proteins refers to groups having 1, 2, 3, 4, or 5 proteins, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

The invention claimed is:

1. A synthetic serous membrane comprising one or more biocompatible polymers that form a topological duplicate at the nano- or micro-scale level, of a donor serous membrane, wherein the topological duplicate is a synthetic pericardial, pleural, or peritoneal membrane, or any combination thereof, wherein the synthetic pericardial, pleural, or peritoneal membrane includes a two-layer membrane, wherein the synthetic serous membrane is free from the donor serous membrane and is formed without collagen.

2. The synthetic serous membrane of claim 1, wherein the one or more biocompatible polymers are selected from the group consisting of agarose, chitin, chitosan, polyglycolic acid, polylactic acid, polylactide-glycolide, and polydioxanone, and any combination thereof.

3. The synthetic serous membrane of claim 1, wherein the topological duplicate is capable of facilitating cellular differentiation, cell attachment, cell growth, cell-sheet growth, tissue growth, tissue engineering, or encasing tissues or organs, or any combination thereof.

4. The synthetic serous membrane of claim 1, wherein the two-layer membrane includes a synthetic visceral and parietal layer.

5. The synthetic serous membrane of claim 1, wherein the one or more biocompatible polymers are selected from the group consisting of poly(hyaluronic acid); poly(sodium alginate); poly(ethylene glycol); poly(urethanes); poly(siloxanes); poly(ethylene); poly(vinyl pyrrolidone); poly(2-hydroxy ethyl methacrylate); poly( N-vinyl pyrrolidone); poly (methyl methacrylate); poly(vinyl alcohol); poly(acrylic acid); poly(vinyl acetate); polyacrylamide; poly(ethylene-co-vinyl acetate); poly(methacrylic acid); nylons; polyamides; polyanhydrides; poly(ethylene-co-vinyl alcohol); polycaprolactone; polyvinylhydroxide; poly(ethylene oxide) and any combination thereof.

6. A method for producing a synthetic serous membrane comprising:
adding one or more biocompatible polymers to a topological imprint of a donor serous membrane, wherein the imprint is a synthetic pericardial, pleural, or peritoneal membrane imprint, or any combination thereof, and wherein the synthetic pericardial, pleural, or peritoneal imprint includes a two-layer imprint, to form a synthetic serous membrane comprising one or more biocompatible polymers that form a topological duplicate of the donor serous membrane at the nano- or micro-scale level, wherein the topological duplicate is a synthetic pericardial, pleural, or peritoneal membrane, or any combination thereof, wherein the synthetic pericardial, pleural, or peritoneal membrane includes a two-layer membrane; and
removing the synthetic serous membrane from the imprint, wherein the synthetic serous membrane is free from the donor serous membrane and is formed without collagen, thereby producing the synthetic serous membrane comprising a topological duplicate of the donor serous membrane.

7. The method of claim 6, wherein the one or more biocompatible polymers are selected from the group consisting of agarose, chitin, chitosan, polyglycolic acid, polylactic acid, polylactide-glycolide, and polydioxanone, and any combination thereof.

8. The method of claim 6, wherein the two-layer imprint is an imprint of a synthetic visceral and parietal layer.

9. The method of claim 6, wherein the one or more biocompatible polymers is a different polymer than a polymer used to form the imprint.

10. The method of claim 6, wherein the removing is by physical, enzymatic, or chemical methods.

11. The method of claim 10, wherein the physical method is by a change in temperature or pressure, or both.

12. The method of claim 6, wherein the imprint remains intact following the removing.

* * * * *